United States Patent
Anello et al.

[11] Patent Number: 5,964,802
[45] Date of Patent: Oct. 12, 1999

[54] ADJUSTABLE INTRAOCULAR LENS

[75] Inventors: Robert Anello, Marina del Rey, Calif.; Ali Amiry, Chicago, Ill.

[73] Assignee: Quantum Vision, Inc., Chicago, Ill.

[21] Appl. No.: 09/018,402

[22] Filed: Feb. 4, 1998

Related U.S. Application Data

[62] Division of application No. 08/592,845, Jan. 22, 1996, Pat. No. 5,728,155.

[51] Int. Cl.$^6$ ........................................................ A61F 2/16
[52] U.S. Cl. .................................................................. 623/6
[58] Field of Search ................................................... 523/6

[56] References Cited

U.S. PATENT DOCUMENTS

| | | |
|---|---|---|
| 4,249,271 | 2/1981 | Poler . |
| 4,268,921 | 5/1981 | Kelman . |
| 4,512,039 | 4/1985 | Lieberman . |
| 4,573,998 | 3/1986 | Mazzocco . |
| 4,575,373 | 3/1986 | Johnson . |
| 4,619,662 | 10/1986 | Juergens, Jr. . |
| 4,638,056 | 1/1987 | Callahan . |
| 4,685,920 | 8/1987 | Fritch . |
| 4,685,921 | 8/1987 | Peyman . |
| 4,693,716 | 9/1987 | Mackool . |
| 4,693,717 | 9/1987 | Michelson . |
| 4,702,244 | 10/1987 | Mazzocco . |
| 4,709,996 | 12/1987 | Michelson . |
| 4,710,193 | 12/1987 | Volk . |
| 4,713,072 | 12/1987 | Bowald . |
| 4,715,373 | 12/1987 | Mazzocco . |
| 4,720,286 | 1/1988 | Bailey . |
| 4,725,278 | 2/1988 | Shearing ...................................... 623/6 |
| 4,731,078 | 3/1988 | Stoy . |
| 4,764,169 | 8/1988 | Gerndahl . |
| 4,769,034 | 9/1988 | Poley . |
| 4,787,903 | 11/1988 | Grendahl . |
| 4,790,847 | 12/1988 | Woods . |
| 4,813,954 | 3/1989 | Siepser . |
| 4,816,031 | 3/1989 | Pfoff . |
| 4,819,631 | 4/1989 | Poley . |
| 4,822,359 | 4/1989 | Tano . |
| 4,842,601 | 6/1989 | Smith . |
| 4,878,910 | 11/1989 | Koziol et al. . |
| 4,888,012 | 12/1989 | Horn . |
| 4,932,966 | 6/1990 | Christie . |
| 4,955,904 | 9/1990 | Atebara . |
| 4,994,082 | 2/1991 | Richards . |
| 5,066,301 | 11/1991 | Wiley . |
| 5,108,429 | 4/1992 | Wiley . |
| 5,171,266 | 12/1992 | Wiley . |
| 5,171,319 | 12/1992 | Keates . |
| 5,173,723 | 12/1992 | Volk . |
| 5,178,622 | 1/1993 | LEhmer . |
| 5,203,668 | 4/1993 | Marmur . |
| 5,203,788 | 4/1993 | Wiley ........................................... 623/6 |
| 5,222,981 | 6/1993 | Werblin . |
| 5,275,624 | 1/1994 | Hara . |
| 5,288,293 | 2/1994 | O'Donnell, Jr. . |
| 5,290,892 | 3/1994 | Namdaran . |
| 5,300,115 | 4/1994 | Py . |
| 5,326,347 | 7/1994 | Cumming . |
| 5,326,348 | 7/1994 | Nordan . |
| 5,344,447 | 9/1994 | Swanson . |
| 5,344,448 | 9/1994 | Schneider . |
| 5,358,520 | 10/1994 | Patel . |
| 5,384,606 | 1/1995 | Koch . |
| 5,391,202 | 2/1995 | Lipshitz . |
| 5,443,506 | 8/1995 | Garabet . |
| 5,466,260 | 11/1995 | Silvestrini . |

OTHER PUBLICATIONS

Martin et al, editors, Foldable Intraocular Lenses, 1993, Chapters 5–7, and 9.

Sabbagh, Leslie, "Multipiece IOL Seen as Refractive Tool," Ophthalmology Times, Jan. 30–Feb. 5, 1995, p. 14.

Primary Examiner—Michael J. Milano
Attorney, Agent, or Firm—Niro, Scavone, Haller & Niro

[57] ABSTRACT

Improved adjustable intraocular lenses are disclosed, in which the optic(s) can be rotated post-operatively using manual methods; controlled pulses of laser radiation or micromotors to achieve improved focus and astigmatic correction.

4 Claims, 5 Drawing Sheets

ADJUSTABLE INTRAOCULAR LENS

This application is a divisional of application Ser. No. 08/592,845, now U.S. Pat. No. 5,728,155 filed on Jan. 22, 1996.

BACKGROUND OF THE INVENTION

1. Field of the Invention

This invention relates to improved intraocular lenses which can be adjusted to correct both spherical and cylindrical refractive errors following implantation. The intraocular lens assemblies (IOL's) of this invention may be foldable to enable implantation with minimal trauma to the eye.

2. Description of the Prior Art

The lens of a normal human eye is situated more or less centrally behind the pupil. A normal lens is substantially symmetrical, with opposed convex surfaces. Both the lens and cornea which protects it refract incoming light to focus it on the retina. The total refraction of the eye is approximately 60 diopters. The lens supplies approximately 20 diopters of correction, while the cornea provides about 40 diopters.

When a cataract forms, the lens becomes progressively opaque and eventually has to be surgically removed, typically through a horizontal incision on the sclera or the cornea itself. Removal of the lens, however, drastically changes the focal point of the light impinging on the retina, resulting in inability to focus a clear image. Correction of focus using eyeglasses and contact lenses, or a combination thereof, is often not fully satisfactory. Eyeglasses can lead to double vision, while contact lenses require periodic replacement which may be beyond the manual skills of elderly patients in whom cataracts most frequently appear.

Prior art intraocular lenses provide a partial solution to these problems. Such lenses in the past have comprised fixed focus devices made of rigid plastic or soft, foldable materials. They are implanted via the corneal or scleral incision through which the cataract was removed, by folding the IOL (in the case of foldable designs) and inserting it into the eye behind the pupil. The IOL may then unfold and is maneuvered into place through the incision. Typically, the fixed focus IOL comprises a central optic fitted with hook-shaped haptics which attach the IOL to the walls of the posterior chamber of the eye. (Placement of the IOL within the anterior chamber is also possible in some instances). The simplest optic surface is a spherical section. IOL's also may be made having optics with asymmetrical curvature designed to correct for astigmatism. This is accomplished by creating an optic in which the curvature is different along axes at 90° apart.

Since the shapes of individual eyes vary, fixed focus IOL's must be custom made for each patient. This requires pre-operative measurement of the axial length of the eye and the curvature of the cornea; prediction of the position of the IOL in the eye after implantation, and pre-operative calculation of the proper IOL power using available formulas. Such predictions, however, are not always accurate. The shape of the eye may be changed as a result of the surgical procedure and subsequent post-operative healing process. Moreover, in the case of asymmetrically curved optic surfaces that are designed to correct for astigmatism, the desired angular orientation of the IOL within the eye may not be perfectly achieved during implantation. In fact, the desired angular orientation can change during the post-operative healing period. So can the placement of the IOL along the optical axis of the eye, which changes the effective focus of the optic. These factors are aggravated in pediatric patients, whose eyes are still changing shape as the patient grows.

Various techniques, both extracorporeal and inside the eye, have been suggested for post-operative adjustment of focus. Small adjustments of the angular orientation of the IOL may be made shortly after surgery using a needle inserted through the paracentesis incision at the corneoscleral limbus before the IOL has been fully fixated within the capsular bag via capsular fibrosis. But, the IOL may subsequently rotate away from the revised position and at this point in time the post-operative keratometric axis typically has not yet stabilized.

Eyeglasses or contact lenses can correct for residual spherical and/or cylindrical error, thereby allowing the post-operative cataract surgery patient to achieve optimal vision. In extreme cases invasive secondary surgical procedures such as radial, astigmatic or photorefractive keratotomy may be required. Sometimes, the IOL must be replaced, or secondary IOL's must be implanted.

The three types of post-operative adjustments of an IOL that may be desired are (1) changes of the axis of astigmatic correction, which is determined by the angular orientation of the IOL; (2) changes of the cylinder magnitude accompanying the astigmatism correction; and (3) changes of the spherical power due to imprecise prediction of the power of the IOL for a particular patient's eye. Adjustment of spherical power can be accomplished by movement of the optic along the axis of the eye; by changing the curvature of the optic, or by adjusting the index of refraction of the optic material.

Various techniques have been suggested for altering the sphero-cylindrical corrective power of IOL's. U.S. Pat. No. 5,443,506 (Garabet), for example, discloses an IOL comprising a fluid-filled lens whose focus can be changed by pumping fluids of differing refractive indices into and out of the central optic; pumping is effected by the response of various types of ioric fluids to electrical potentials generated when the ciliary body expands or contracts. U.S. Pat. No. 5,066,301 (Wiley) describes a variable focus intraocular lens comprising an envelope filled with a transparent gel in which are suspended a plurality of light-reflective particles. The orientation of the particles is said to be controllable by application of an electromagnetic or other force field, thus providing both variable spherical power and some post-operatively adjustable correction for astigmatism.

U.S. Pat. No. 4,787,903 (Grendahl) describes an IOL comprising a fresnel-type lens overlaid by a crystalline or other material that changes index of refraction when excited by electrical power or radiant energy, thus providing a post-operative adjustment function. In U.S. Pat. No. 4,816,031 (Pfoff), an IOL assembly comprising a hard PMMA (polymethyl methacrylate) optic overlain by a soft silicon optic is disclosed. The focal length of the optic assembly is adjustable by microfluid pumps that adjust the volume of clear fluid encapsulated between the PMMA optic and the silicon optic, thus changing the distance between the two optics and thereby altering the focus of the optic assembly.

U.S. Pat. No. 5,108,429 (Wiley) discloses a non-foldable IOL assembly in which a rigid hoop surrounds a fixed-focus optic. The hoop is fixed in the eye by means of external haptics; the optic is attached to the hoop by a plurality of micromotor devices illustrated as pistons which are said to be able to move the optic back and forth with respect to the hoop in response to computer-controlled electrical signals. U.S. Pat. No. 5,203,788 (Wiley) describes a non-foldable IOL assembly in which a rigid outer ring or hoop surrounds an inner optic; the optic is operatively attached to a helical groove in the outer ring via a plurality of micromotors which are said to be operable to adjust the focus or power of the IOL assembly by changing the distance of the optic from the retina.

U.S. Pat. No. 4,944,082 (Richards, et al.) discloses an IOL assembly comprising a pair of optics hinged at one portion of their circumferences and operatively attached to the ciliary muscle at an opposing portion of their circumferences, so that expansion or contraction of the ciliary muscle changes the distance between the optics and thereby the focus of the assembly. In U.S. Pat. No. 4,790,847 (Woods), a capsule assembly surrounds an optic which is attached to the ciliary muscle. Movement of the muscle urges the optic against the anterior wall of the capsule with more or less force, thus changing the focus of the overall assembly.

U.S. Pat. No. 5,288,293 (O'Donnell) discloses an intraocular lens comprising a layer or series of layers of materials which respond to the application of laser energy, forming microfenestrations by collapsing, thus altering the front curvature of the lens. And U.S. Pat. No. 4,575,373 (Johnson) discloses a laser adjustable IOL especially designed for post-operative correction of astigmatism, in which the lens comprises an outer ring made of heat-shrinkable plastic. The plastic is colored to permit selective absorption of laser energy. The IOL is adjusted post-operatively by focusing laser energy on parts of the outer ring, causing selective shrinkage and warping the optic to create the desired variation between curvatures along the vertical and horizontal meridians.

Generally speaking, therefore, prior art approaches to achieving post-operative adjustment of the focussing capability of an IOL, therefore, have required movement of fluid into, out of or within an IOL assembly; micromotor-actuated adjustment of the position of optics operatively mounted within rigid hoops or rings; refractive index adjustment in response to externally-applied energy, or one-time, irreversible warping of an optic held inside a rigid ring by selective application of laser energy to parts of the surrounding ring.

SUMMARY OF THE INVENTION

It is an object of this invention to provide an IOL that can be adjusted post-operatively to alter its power so as to minimize the residual spherical error of the eye.

It is another object of this invention to provide an IOL that can be adjusted post-operatively so as to correct astigmatism.

It is a further object of this invention to provide an adjustable IOL that can be foldable, for easy implantation with minimum trauma.

It is yet another object of this invention to provide an IOL that can be adjusted post-operatively so as to alter both spherical and astigmatic errors that were either present prior to surgery or that may develop during the healing period following cataract surgery.

It is a further object of this invention to provide an adjustable IOL that can be adjusted post-operatively using standard surgical tools such as those described in U.S. Pat. No. 4,573,998 (Mazzocco), and without need for micromotors, computers or other machinery implanted within the eye itself.

It is a related and additional object of this invention to provide methods for post-operative adjustment of the IOL's of this invention based on calculations from keratometric measurements.

It is still another object of this invention to provide an IOL that can be adjusted post-operatively using non-invasive pulsed laser radiation, and in which such adjustment can be made repeatedly in any desired direction.

It is yet a further object of this invention to provide an adjustable IOL that allows a wide range of focus adjustments, including if desired adjustments to correct astigmatism, while maintaining a shallower profile within the eye than has heretofore been attainable.

It is still another object of this invention to provide micromotor-actuated post-operative adjustable or accommodating IOL assemblies that can be non-rigid and that, as a result, can be implanted with minimal trauma.

It is a further and related object of this invention to provide simple micromotor-operated accommodating IOL assemblies using only one micromotor.

These and other objects of our invention are achieved by providing intraocular assemblies incorporating axial focus capability via post-operative manual rotation of a spherical optic mounted in a soft haptic body having a circular helical thread, using an instrument inserted through the paracentesis incision at the corneo-scleral limbus. Post-operative adjustment for correction of astigmatism can be achieved by manual rotation of an optic having variable power along meridians separated by 90°, again using a needle or other instrument. In some embodiments of our invention, the rotatable optic comprises a fluid- or gel-filled flexible capsule fitted to rotate within the confines of a helical groove of progressively diminishing diameter; thus, axial movement also changes the curvature of the optic, resulting in more-rapid adjustment of power compared to an optic of fixed shape. This arrangement results in an IOL assembly that is shallower than otherwise would be possible. In other embodiments of our invention, rotation of the optic for purposes of adjustment of spherical power or astigmatic correction is accomplished by shock waves generated against vanes using pulses of laser light. In still other embodiments of our invention, a single micromotor is used to move an optic axially within a haptic assembly, which may be foldable or non-rigid.

DETAILED DESCRIPTION OF THE PREFERRED EMBODIMENTS

Intraocular Lens Assembly Manually Adjustable for Astigmatic Correction (Angular Orientation)

Figures 1, 2:
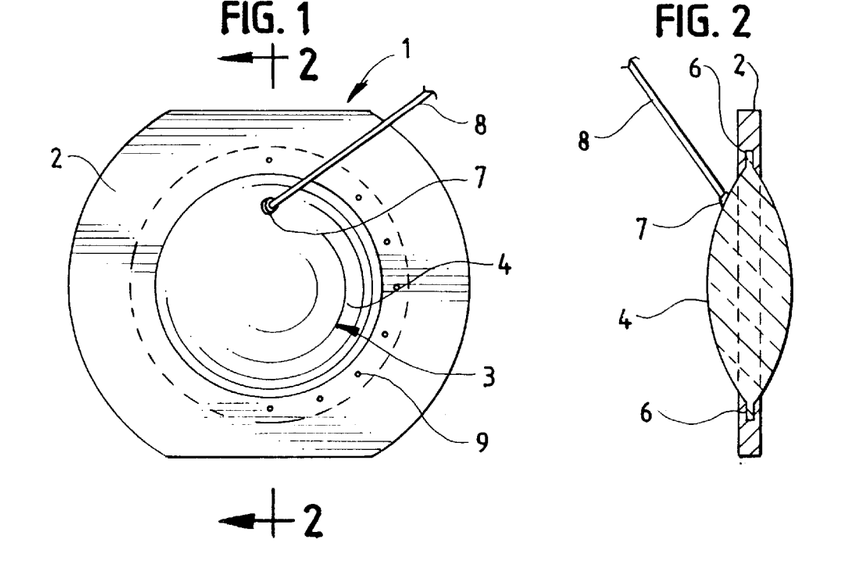
FIG. 1 shows an IOL based on our invention which can be manually adjusted post-operatively to alter the astigmatic correction.
FIG. 2 shows a cross section 2—2 of the IOL of FIG. 2.

FIG. 1 illustrates an embodiment of our invention designed to allow post-operative adjustment to more fully correct astigmatism. The IOL comprises a haptic 2, preferably having the general shape of an oval or truncated oval with a major axis of approximately 10 to 11 mm and a minor axis of about 8 to 10 mm. The haptic includes a central aperture 3 which is about 5 to 7 mm in diameter and which accommodates the optic 4, illustrated in FIG. 2. The haptic is preferably formed as a continuous piece of soft, foldable material. The periphery of the optic includes an integral flange 5, which is 1 to 2 mm in width and 0.1 to 0.5 mm in thickness and which is designed to fit within a circular groove 6 surrounding the aperture 3 in the haptic 2. The flange 5 fits within the circular groove 6 snugly enough to provide stability, but loosely enough to enable rotation of the lens 4 by means of force manually applied to attachment member 7. Attachment member 7 may comprise a depression or notch in the flange 5 or optic 4 designed to accommodate an adjustment probe 8; alternatively a loop of plastic may be attached to accommodate a hook-shaped or pointed adjustment probe. Optionally, a plurality of calibration markings 9 may be incised on the surface of haptic 2 at regular intervals around the periphery of the aperture 3.

Post-operative adjustment to optimize astigmatic correction can be accomplished at approximately 6 to 12 weeks after initial surgery. At this point in time, the IOL is fixated or fibrosed in place within the capsular bag, and the corneal astigmatism of the eye has stabilized. Adjustment of astigmatic correction is accomplished by physical rotation of the optic 4 within the haptic 2 until the cylindrical correction of the lens is oriented in the ideal position. The adjustment probe 8 is inserted through the paracentesis incision at the corneo-scleral limbus for that purpose. A second probe can be inserted through a second paracentesis incision to hold the haptic body firmly in place as optic 4 is rotated.

To determine the desired extent of rotation, a keratometric reading is made of the eye before the adjustment. To a first approximation, alignment of the plus cylinder axis of the optic 4 to the steep postoperative keratometry reading of the cornea will provide optimal outcome for many patients. But, the steep postoperative keratometry reading is not always exactly predictive of the residual refractive cylinder of the eye. The actual residual refraction can depend on additional factors such as the pupil size of the eye and the patient's desire or preference for correction of the remaining astigmatism. Also, keratometry measures the curvature of the cornea at a very specific radial position, that of the 3 mm optical zone, which may not be indicative of the overall shape of the cornea that is responsible for forming images. Thus, in some patients, there will be an inherent discrepancy between the measured corneal curvature and the residual refractive astigmatism of the eye which is independent of, and in addition to, measurement error.

If alignment of the plus cylinder axis of the central optic of the present invention to the steep postoperative keratometry reading does not provide optimal outcome then vector analysis of the postoperative keratometric astigmatism, the postoperative residual refractive cylinder, and the postoperative orientation of the plus cylinder of the optic can be employed to estimate the optimal orientation of the optic. More specifically, in an ideal situation the keratometric astigmatism of the eye ($\vec{K}$) and residual refractive astigmatism of the eye ($\vec{R}$) would inherently correspond in magnitude and angular orientation, so that $\vec{R} = \vec{K} + \vec{I}$, where the vector quantities $\vec{K}$, $\vec{R}$ and $\vec{I}$ (the IOL optic itself) are expressed in cylindrical notation with magnitudes in diopters and orientations expressed in degrees relative to the horizontal. In real situations, however, to achieve optimal orientation of the lens a vector offset correction factor $\vec{a}$ may be introduced in order to arrive at the actual residual refractive astigmatism:

$$\vec{R} = \vec{K} + \vec{I} + \vec{a}$$

In this equation, what is known are the magnitude and orientation of $\vec{R}$ (determined by refracting the patient post-operatively), $\vec{K}$ (by keratometric measurement) and $\vec{I}$ (magnitude by specification determined before installation of the lens, and angular orientation by post-operative measurement). The vector offset factor $\vec{a}$ is calculated as follows:

$$\vec{a} = \vec{R} - (\vec{K} + \vec{I})$$

The offset factor a remains constant for a particular eye and is used to calculate a modified post-operative keratometric astigmatism $\vec{K}'$ as follows:

$$\vec{K}' = \vec{K} + \vec{a}$$

The plus cylindrical axis of the optic should be rotated to the orientation determined by the angle of $\vec{a}$ plus or minus 90° to provide an improved estimate of the optimum alignment of the plus cylinder axis of the central optic. This adjustment can be further improved by actually refracting the patient during the postoperative adjustment procedure. That procedure comprises performing fine adjustments to the lens while the patient views a standard eye chart used to measure visual acuity. As the physician slightly alters the positions of the lens or lenses, the patient is asked which configuration produces the best vision. In this way, the final adjustment may be arrived at in a very precise manner.

Figure 3:
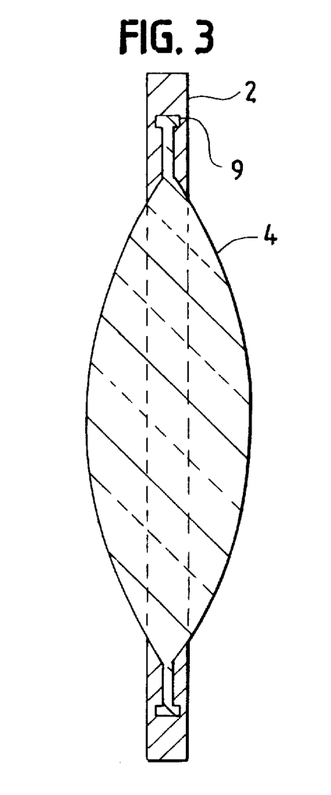
FIG. 3 shows an alternate cross section 2—2 of the IOL of FIG. 2.
Figure 4:
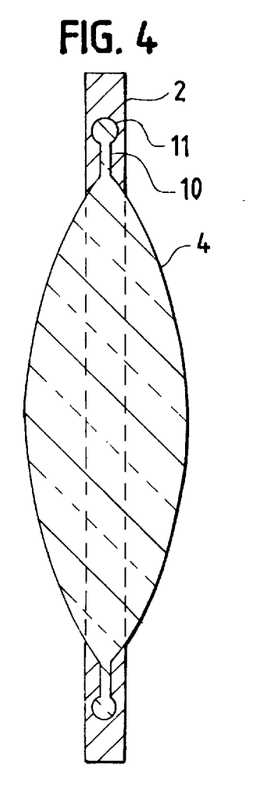
FIG. 4 shows another alternate cross section 2—2 of the IOL of FIG. 2.

A variety of flange shapes may be used to retain the lens 4 in the haptic 2. FIG. 3 shows a flange 9 having a T-shaped cross section, which is useful in retaining the optic within the haptic during the implantation and rotation processes. FIG. 4 illustrates a flange 10 comprising a portion 10 that appears flat in cross section and that attaches the periphery of the optic 4 to a doughnut-shaped element 11. Again, this shape is useful to help retain the optic within the haptic during the implantation process and during rotation.

Figure 5:
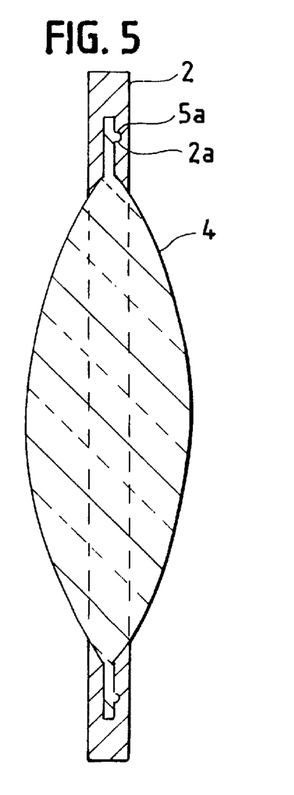
FIG. 5 shows a detail of certain optional features of the circular groove and flange arrangement.

It may be desirable to provide a plurality of depressions 2A around one or both faces of circular groove 6, together with a single protrusion 5A on one or both surfaces of flange 5. See FIG. 5. As the optic 4 is rotated, the protrusion(s) 5A sequentially engages the depressions 2A by slightly deforming haptic 2 when the protrusion(s) is between depressions. This provides added protection against unintentional rotation of the optic after the adjustment procedure is finished.

Intraocular Lens Assembly Manually Adjustable for Focus (Power)

Figure 6:
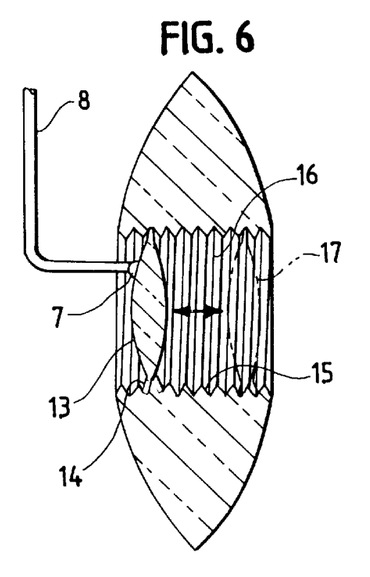
FIG. 6 illustrates a cross section of an IOL of our invention which can be manually adjusted post-operatively to alter its spherical correction (power).

To adjust the power of the IOL (that is, its ability accurately to focus near and far objects on the retina) using a spherical optic of constant shape in the absence of astigmatism, it is necessary to move the optic along the axis of the eye. FIG. 6 illustrates an embodiment of our invention that accomplishes this. The haptic 12 is preferably foldable and preferably lozenge-shaped in cross section, having a maximum thickness of slightly more than 4 mm to allow for translational movement of the optic over a 4 mm long path. This provides a postoperative adjustment range of about ±2.5 diopters at the spectacle plane, which is sufficient in most instances to allow correction of post-operative residual spherical error in most patients. The preferred dimensions of the haptic in plan view are similar to the dimensions noted above for the IOL of FIG. 1.

The haptic 12 is preferably hollow, foldable and lozenge-shaped. In addition to the haptic 12, the embodiment of FIG. 6 preferably comprises a soft, foldable optic 13 (preferably of spherical conformation) fitted with a flange 14 which engages a continuous circular helical groove 15 at the inner periphery of the aperture 16 in the haptic 12. The optic may be plano on one side and convex on the other or biconvex or concave in some instances. When the optic 13 is rotated using an adjustment tool 8 to engage an attachment member 7, the optic 13 moves axially backward or forward within the aperture 16. (A second position of the optic is shown at 17 in phantom lines.) Also, stops are preferably provided at each end of the helical groove 15 to prevent the optic from becoming detached from the helical groove as a result of excessive rotation in either direction.

Figure 7:
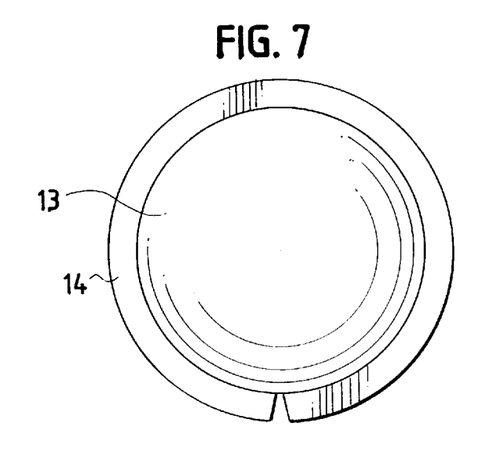
FIG. 7 shows the optic portion of an IOL of one embodiment of our invention, illustrating the shape of the flange that is required to maintain the optic perpendicular to the axis of the eye.
Figure 8:
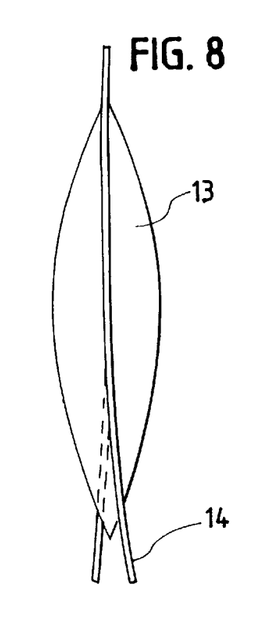
FIG. 8 illustrates a side view of the optic of FIG. 7.

FIGS. 7 and 8 illustrate a preferred configuration of flange 14 in greater detail. Although the flange 14 may be a flat or angled disc, it preferably should match the helical shape of the groove in order to maintain the plane of the optic more nearly perpendicular to the optical axis of the eye. Such a flange will have the shape of a single flight of a helical screw, as shown in FIGS. 7 and 8. Alternatively, flange 14 may be helical and further comprise a T-shaped section as in FIG. 3 or a doughnut-shaped section as in FIG. 4.

The IOL of this embodiment is preferably, though not necessarily foldable. Folding before implantation may be accomplished by first collapsing the thickness of the lens so as to collapse the central threaded cylindrical region about the central optical element(s). The resulting configuration is then rolled, then evacuated via exterior positioning holes (not shown) which are then sealed. The folded device is then packaged for sale to the surgeon. The surgeon then injects the IOL and maneuvers it into the capsular bag in the usual manner. Once oriented properly in place, the sealed positioning holes are punctured with a needle and the IOL thereby absorbs aqueous from the anterior chamber and fills to capacity.

Figure 9:
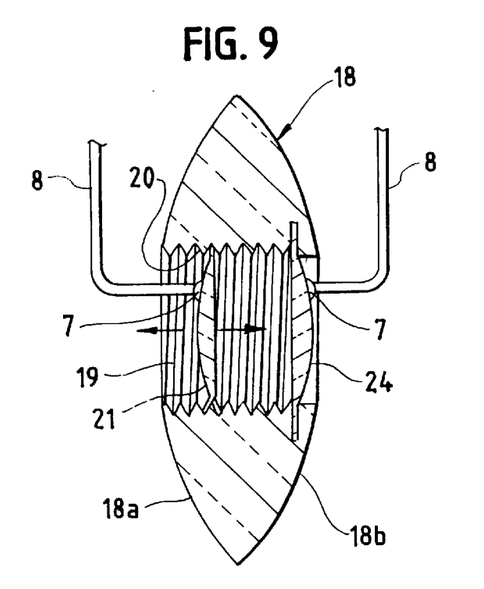
FIG. 9 illustrates a cross section of an IOL of our invention which can be adjusted post-operatively to alter both astigmatic and spherical correction.

Intraocular Lens Assembly Manually Adjustable to Alter Both Spherical Power and Astigmatic Correction FIG. 9 illustrates a cross section of another embodiment of our invention in which both spherical power and astigmatic correction can be manually adjusted after implantation. This embodiment comprises a haptic 18 generally shaped and sized like the embodiment of FIG. 6, but slightly thicker. The haptic has an anterior surface 18a and a posterior surface 18b. Around the periphery of aperture 19 is a continuous circular helical groove 20 extending from the surface of the IOL that faces the cornea to a point approximately 4 mm back toward the retina—that is, toward the posterior surface 18b of the haptic. A first, focusing optic 21, which is preferably biconvex or plano-convex in conformation, is fitted with a flange 22 to engage the circular helical groove 20. The spherical power of the IOL is adjusted post-operatively as in the embodiment of FIG. 6 by rotating the first focusing optic 21 using an adjustment tool 8 to engage an attachment member 7.

In addition to first focusing lens 21, the embodiment of FIG. 9 comprises a second planar groove 23 situated close to the posterior surface 18b of the haptic. The second planar (disc-shaped) groove accommodates the flange 25 of a second toric optic 24, which has different power along two meridians or axes 90° apart and is used to correct astigmatism. Second toric optic 24, which may be plano-convex, is situated near the surface of the IOL that faces the retina, is adjusted postoperatively as described in connection with the embodiment of FIGS. 1–5. Optionally, the edge of flange 25 can be any of the shapes disclosed in connection with the embodiment of FIGS. 1–5, including circular or T-shaped. Some provision is preferably made for venting aqueous humor from one side to the other of optic 21 as it moves axially along helical groove 20.

To avoid having to obtain access to both faces of the IOL, a sleeve of the type described below in connection with the embodiment of FIG. 22 can be used.

Thus, this embodiment permits post-operative change in both the spherical and astigmatic correction provided by the IOL. As with the embodiments described above, such post-operative adjustments can be made as frequently as necessary throughout the life of the IOL.

Post-Operative Adjustment Using Non-Invasive Pulsed Laser Radiation

Figure 10:
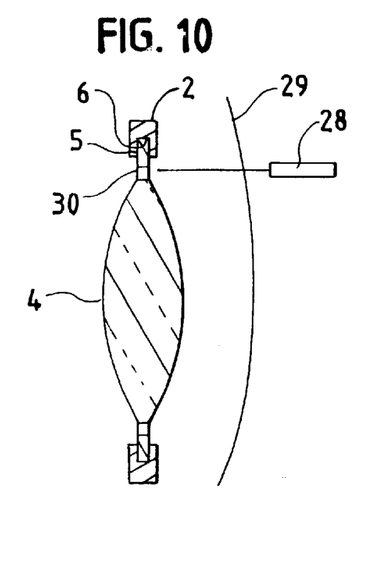
FIG. 10 shows a cross-section of an embodiment of our invention which can be rotated by means of laser radiation.

The foregoing embodiments also can be adapted to allow postoperative adjustment using a non-invasive laser procedure. FIG. 10 illustrates a cross section of an embodiment similar to the astigmatism-correcting IOL of FIGS. 1–5, except that the lens further comprises at least one angled target or vane 30 attached to or formed on the flange 5, or within the periphery of the optic 4. When the angled vane 30 is struck by a brief pulse of focused laser radiation from laser source 28, aimed through the cornea 29, the laser radiation creates a plasma by stripping electrons at the site of focus. Creation of the plasma generates an outwardly expanding spherical shock-wave (in all directions). Angulation of the vane transfers some of the normally incident energy of the spherical shock-wave into rotational motion. The use of controlled pulses allows fine adjustment of the optic position.

Preferably, a Nd:YAG laser is used, rather than a visible laser. The UV radiation produced by the Nd:YAG laser is not absorbed by the intervening optically clear cornea and aqueous humor, so substantially all of its energy is transferred directly to the vane. It will be appreciated that this technique avoids even the minor surgical procedure required to insert a manipulating tool to adjust the position of the optic manually, as described above.

Figure 11:
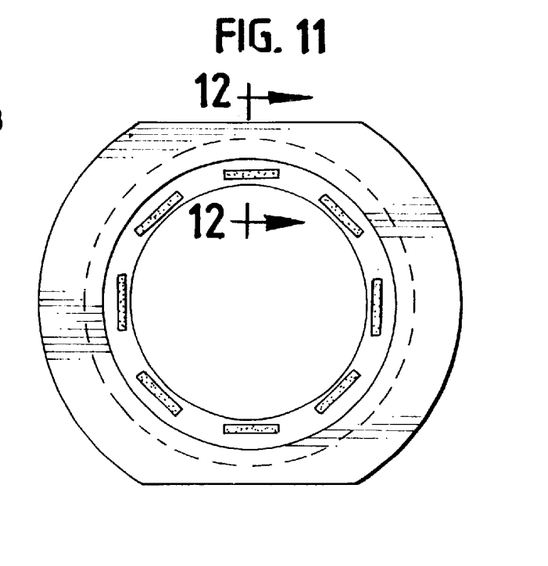
FIG. 11 shows a plan view of the optic used in the IOL of FIG. 10.
Figure 12:
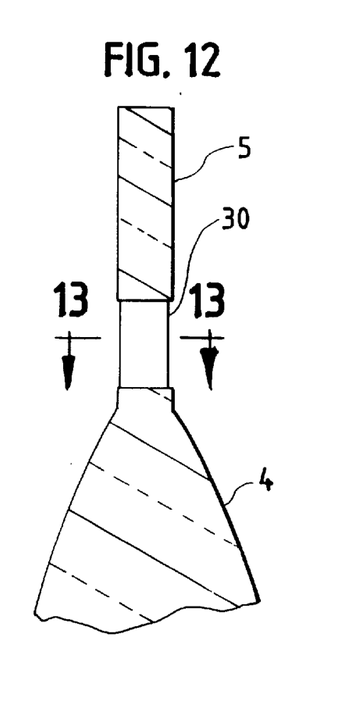
FIG. 12 shows an enlarged partial cross section 12—12 of the optic of FIG. 11.
Figure 13:
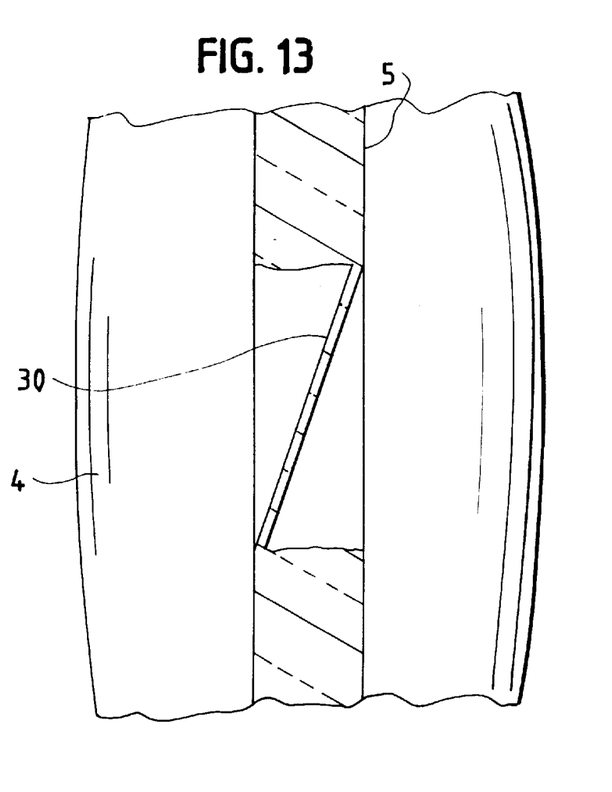
FIG. 13 shows an enlarged partial cross-section 13—13 of the optic of FIG. 12.

FIG. 11 illustrates a front view of a laser-adjustable IOL. As shown, flange 5 of optic 4 further comprises a plurality of angled vanes 30. FIG. 12 illustrates an enlarged cross section of the lens of this embodiment along section line 12—12. And FIG. 13 shows an additional, enlarged cross section along section line 13—13, illustrating angling of the vane(s).

All of the vanes or targets may be angled in the same direction, making it possible to rotate the optic in only one direction. Optionally, and preferably, some of the vanes may be arranged to slant in opposite directions, thus enabling the optic to be rotated either clockwise or counterclockwise depending upon which vane is targeted by the laser.

It will be apparent to those of ordinary skill in the art that using alternately-angled vanes (or for that matter, at least two targets or vanes having opposite angles) would also permit laser adjustment for spherical power in an embodiment similar to that of FIG. 6. In such instance, the vanes or targets are also attached to or formed in the flange or periphery of the optic, and rotation of the lens in either direction is accomplished by striking a vane having the desired angulation with a laser beam. Since the flange runs in a helical groove, the result is axial movement of the optic to adjust its spherical power.

Figure 14:
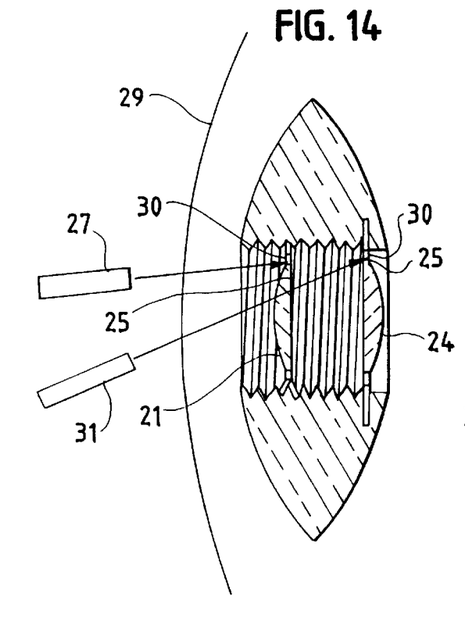
FIG. 14 shows a cross-section of an embodiment of our invention in which both spherical and astigmatic correction may be altered by application of laser radiation.

Referring now to FIG. 14, it can be seen that a two-optic embodiment like that of FIG. 9 also can be adapted for laser adjustment. In such case, the first, focusing optic 21 is fitted with a plurality of vanes 30 as shown in FIGS. 10–13. Some oppositely-angled targets or vanes must be used to permit rotation in either direction. Laser 27 is used as described above to rotate first, focusing optic 21 causing movement axially along helical groove 20. Second, toric optic 24 is also fitted with at least one target or vane 30 attached to its flange 25 or integral to its periphery. Impingement of laser radiation from laser 31 on target or vane 30 causes rotation of second, toric optic 20, thus allowing postoperative adjustment of the astigmatism correction afforded by the IOL.

Intraocular Lens Assembly Adjustable Using a Micromotor

Figure 15:
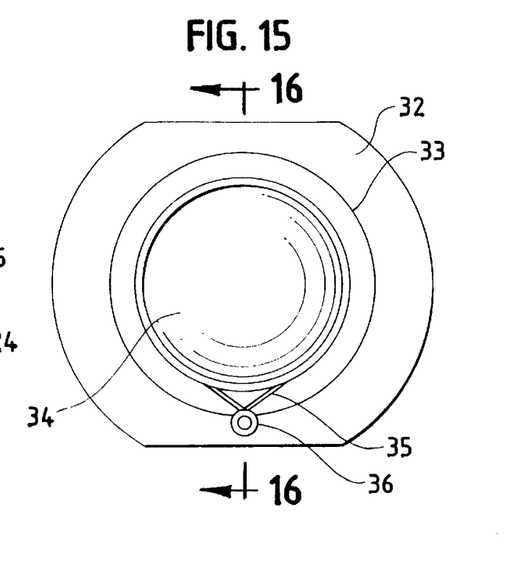
FIG. 15 shows an embodiment of our invention which uses a micromotor to adjust power.

A micromotor device inside the eye also can be used to adjust the optics of intraocular lenses. FIG. 15 shows a front view of such an assembly. Haptic 32 containing aperture 33 is arranged substantially as in the embodiment of FIG. 6. In this embodiment, shown in FIG. 16 in section along section line 16—16, optic 34 is fitted with a flange 35 that engages circular helical groove 36, providing translational movement along the axis of the assembly as described above when lens 34 rotates. A flexible belt 35 operatively connects the periphery of lens 34 with shaft 36 of micromotor 37. The belt 35 preferably is crossed over the micromotor shaft 36 as shown in FIG. 15, to provide better contact with the shaft. Preferably there is higher friction between the belt and the drive. During operation, as shown in FIG. 15, the belt 35 follows the lens back and forth axially through the aperture of the haptic.

Control systems and power source arrangements for micromotors are known in the art (see, e.g., U.S. Pat. Nos. 5,108,429 (Wiley) and 5,066,301 (Wiley) and need not be repeated here.

Figure 17:
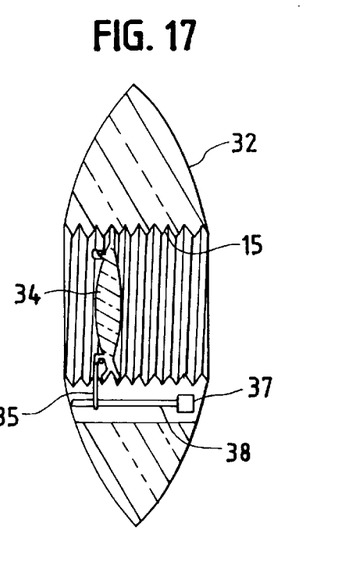
FIG. 17 shows a cross-section of a slightly different version of the embodiment of FIG. 15.

Alternatively, FIG. 17 illustrates an embodiment in which the belt is driven by, and moves along, a motorized screw 38 such that it remains in the same plane as the optic. This eliminates tension and kinking of the belt as the optic moves back and forth.

Figure 16:
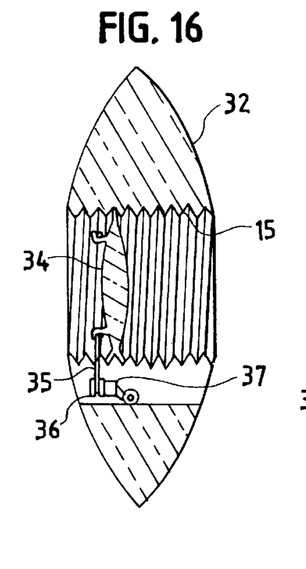
FIG. 16 shows a cross section 16—16 of the IOL of FIG. 15.
Figure 18:
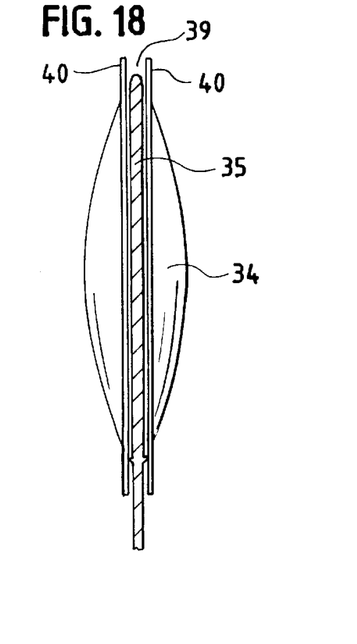
FIG. 18 illustrates a side view detail of the optic portion of the embodiment of FIG. 17.

FIG. 18 illustrates another embodiment in which a pair of flanges 40 are used in place of a single flange to engage the helical groove 15 of FIG. 16 or 17. The pair of flanges 40 forms a trough 39 that helps guide and restrain belt 35, preventing it from slipping off of the optic.

One advantage of belt arrangements such as those shown in FIGS. 15–18 is that only a single micromotor is needed to operate the device, in contrast to prior art proposals that required a plurality of micromotors arranged inside the periphery of a rigid, non-foldable hoop.

It will be understood by those of ordinary skill in the art that the belt and micromotor arrangements of FIGS. 15–18 also can be applied to two-optic systems like the one illustrated in FIG. 9. Two belts and two micromotors are used: one set to rotate and axially translate the first, focusing optic and the second set to rotate the second, toric optic to alter astigmatic correction.

Figure 19:
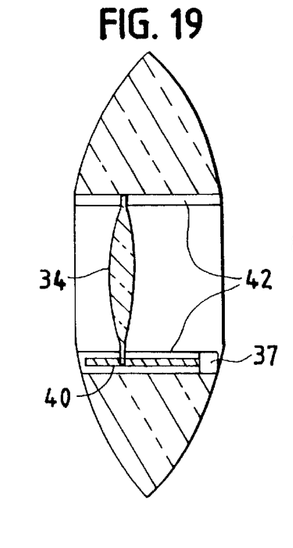
FIG. 19 shows a cross section of an alternate embodiment of our invention using a micromotor to adjust focus.

Still another alternate mechanism for achieving translational motion of the optic is shown in FIG. 19. In this embodiment, a worm gear 40 engages the peripheral flange 41 of optic 34, to provide translational motion of lens 34 which is restrained by flange 41 in slots 42. In this arrangement the optic need not rotate. In a further alternate mechanism, worm gear 40 is replaced by a long, toothed gear which engages teeth on the periphery of the flange of the optic; translation is accomplished as the flange rotates in a helical groove.

Other pulley arrangements are also possible. For example, in place of a circular helical groove, the flange of the optic could travel longitudinally in a plurality of axially-extending tracks or grooves in the aperture of the haptic. A micromotor and pulley arrangement could be used to pull the optic back and forth without having to rotate it.

Adjustment of Spherical Power and Astigmatic Correction Using a Single Lens

Figure 20:
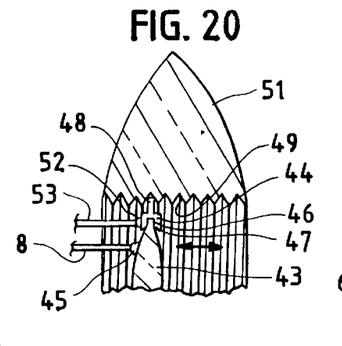
FIG. 20 shows a cross section of another embodiment of our invention designed to allow post-operative adjustment of spherical power and astigmatic correction.

The embodiments of FIGS. 9 and 14 of our invention use two optics: one to adjust spherical power and the other to correct for astigmatism. FIG. 20 shows a cross section of an alternate embodiment that accomplishes both corrections using a single optic 43. The optic 43 is toric; that is, it has varying power along two meridians spaced 90° apart, thereby providing both spherical and cylindrical correction. Accordingly, rotation of the optic 43 using adjustment tool 8 to engage attachment means 45 can alter astigmatic correction. Optic 43 is surrounded by an optic flange 46, which may have any of the profiles shown in FIGS. 3 or 4 or 5, or other appropriate profiles. Flange 46 is supported by a generally torus-shaped traveler 44, which comprises a groove 47 shaped to accommodate optic flange 46 and a helical traveler flange 48 which engages helical groove 49 in aperture 50 of haptic 51. Traveler 44 is also fitted with attachment means 52 to engage adjustment tool 53.

A two-step procedure is used to adjust this IOL assembly. First, spherical correction (power) is adjusted by rotating traveler 44 using adjustment tool 53. During that procedure optic 43 also rotates. When the spherical power has been adjusted properly, adjustment tool 44 is used to rotate optic 43 and its optic flange 46 inside groove 47 of traveler 44. Optionally, calibration markings may be incised upon optic flange 46 to assist in achieving the proper angular orientation of optic 43 for astigmatic correction. During adjustment of spherical power the change in cylindrical power will be negligible.

It will be appreciated that rotation of the optic and traveler of this embodiment also can be accomplished by laser radiation applied to vanes affixed to the optic and traveler, as disclosed above in connection with the embodiments of FIGS. 10–14. Further, a pair of micromotors and belts also could be used to adjust for focus and astigmatism.

Intraocular Lens Assembly Using a Fluid- or Gel-Filled Optic or Optics

When a soft, foldable optic of constant shape that is made of silicon or other appropriate material is used, as in the foregoing embodiments, about 4 mm of axial travel is needed to provide reasonable range of adjustment of spherical power. Thus, the IOL assembly must be somewhat more than 4 mm thick at its thickest point along the optical axis.

Figure 21:
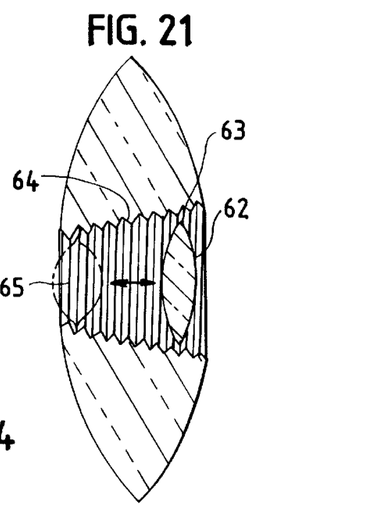
FIG. 21 shows a cross section of an alternate embodiment of our invention using a deformable optic to provide greater variation in power with less translational displacement.

A flexible optic filled with transparent, incompressible fluid having a high index of refraction can be used in an embodiment that allows the overall assembly to be much thinner. As shown in FIG. 21, the fluid-filled lens 62 is fitted with a flange 63 that engages a spiral helical groove 64 of varying diameter. The aperture in the haptic that accommodates the groove is generally frusto-conical in shape, seen in cross-section. As the optic is rotated using any of the techniques and devices described above, the spiral helical groove 64 forces the flange 63 inward or allows it to expand outward. Since the optic comprises a fluid contained in an elastic bag, the radius of curvature of the optic then changes in response to the change in diameter of the spiral helical groove. For example, in a typical eye, an 0.5 mm decrease in diameter of the fluid optic can decrease the radius of curvature by about 2.5 mm, thereby increasing the power by more than 5 diopters. Thus, a given change in power can be accomplished within a much smaller axial movement, since the effect of change in curvature is more efficient, and can be made in addition to translational effects. Alternatively, a conical groove may be used, in which circular grooves are nearly confined to a plane but allow for a sharp curved transition to the next nearly circular groove of lesser diameter. The optic shape and power thus changes in discrete steps as the optic is rotated.

Figure 22:
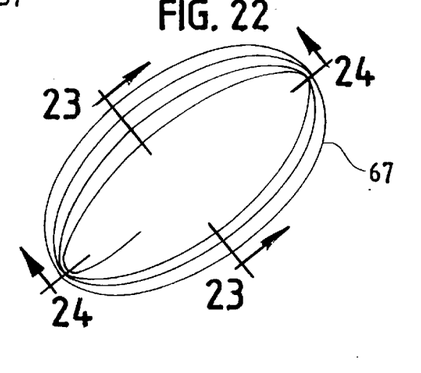
FIG. 22 shows the path of a groove that can be used to alter the cylinder power of the astigmatic correction with a deformable optic.
Figure 23:
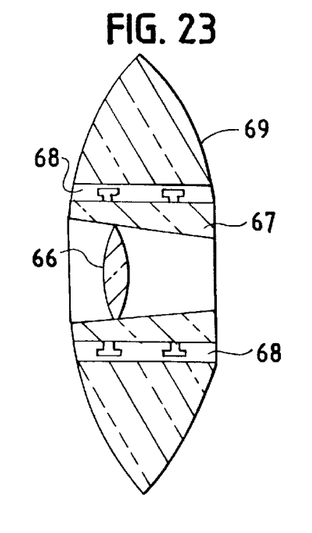
FIG. 23 shows a cross section of an embodiment of our invention using a deformable optic to accomplish post-operative adjustment of both cylinder power and angular orientation of the astigmatic correction.
Figure 24:
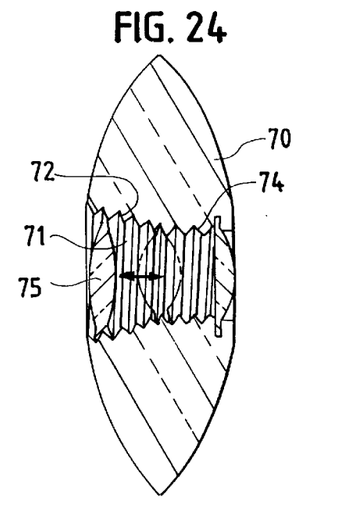
FIG. 24 shows an alternate embodiment of our invention using two deformable lenses to accomplish adjustment of both spherical power and astigmatic correction in a shallower overall design.

Another, alternate embodiment of our invention using a fluid-filled, deformable optic is shown in FIGS. 22–24. In this embodiment, the fluid-filled optic 66 moves along an elliptical spiral helical groove 67 (see FIG. 23) in which the major axis (long axis) is held constant while the minor axis (short axis) is allowed to increase or decrease with the axial movement of the optic along the groove. The cylinder power of the astigmatic correction provided by the optic is thus made to vary since the radius of curvature of the optic is changing in one direction and not the other. In connection with varying the cylinder power of the astigmatic correction by ±1 diopter, the spherical equivalent of the optical surface will change by only ±0.5 diopters. (This change can be counteracted by translation to keep the spherical power approximately constant.)

In this embodiment, provision is also made to allow circular rotation of the entire elliptical helical groove 67 by the addition of a sleeve 68 within the haptic body. The sleeve contains the groove 67 and is allowed to rotate independently within the haptic 69, thereby allowing for adjustment of the angular orientation of the astigmatic correction once the cylinder power is properly set.

In still another embodiment using two fluid-filled optics (see FIG. 24), the haptic 70 is provided with a central aperture divided into a first portion 71 featuring a spiral helical groove 72 of progressively diminishing diameter, and a second portion 73 with an elliptical helical groove 74 of progressively decreasing minor and constant major diameters. First, focusing optic 75 moves within the spiral helical groove to alter the spherical power of the assembly, while second, toric optic 76 moves within the elliptical helical groove to adjust astigmatic correction. Manual adjustment using a tool(s) inserted through the paracentesis incision(s) at the corneo-scleral limbus; laser adjustment or micromotors can be used to rotate the optics.

Embodiments Using Twin Curved Haptics

Figure 25:
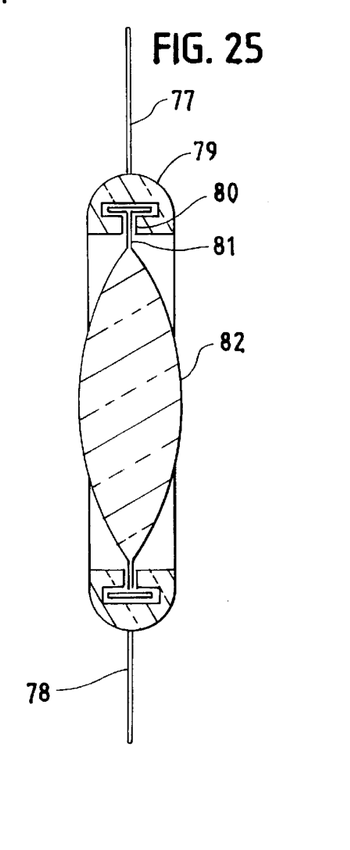
FIG. 25 shows an alternate embodiment of our invention using two curved haptics.

The preceding embodiments have been described as using a single, oval-shaped foldable haptic having a substantially flat or preferably lozenge-shaped profile. FIG. 25 illustrates an alternative embodiment for postoperative adjustment of astigmatic correction that uses a pair of thread-like, curved haptics 77, 78 attached at 180° opposed locations to the exterior surface of a generally toroidal ring 79. (Designs using two separate, curved haptics now account for the majority of sales of all IOL's.)

Toroidal ring 79 comprises a groove 80 on its inner surface to accommodate flange 81 of toric lens 82, which is generally sphero-cylindrical in shape. FIG. 27 shows a T-shaped groove, but it will be understood that grooves of other shapes, as disclosed above, also could be used. Rotation of lens 82 can be accomplished manually or by use of a laser as disclosed above.

In still another alternate embodiment, toroidal ring 79 is thicker along the axis of the eye to accommodate a helical groove. This embodiment enables adjustment of power.

Those of ordinary skill will understand from the foregoing disclosure that many other embodiments can be created that utilize the features of our invention. We intend, therefore, to incorporate all such alternate embodiments and to limit our invention only as set forth in the following claims.

We claim as our invention:

1. An intraocular lens assembly comprising:
   a. a toroidal ring having a substantially circular central aperture;
   b. a groove in said toroidal ring around said central aperture in the plane of said toroidal ring;
   c. an optic having a circular shape with an exterior periphery and a generally sphero-cylindrical conformation suitable for correction of astigmatism, sized to fit within said central aperture;
   d. a flange surrounding said exterior periphery of said optic and extending outward therefrom to operatively engage said groove;
   e. at least one curved, flexible haptic affixed to said toroidal ring and extending outwardly therefrom to provide for retention of said toroidal ring in the eye; and
   f. an attachment member affixed to said flange to enable manual rotation of said optic;

whereby said optic can be rotated within said toroidal ring to alter correction of astigmatism.

2. The intraocular lens assembly of claim 1 wherein said toroidal ring, haptic, optic and flange are foldable to facilitate implantation.

3. The intraocular lens assembly of claim 1 wherein said flange is generally T-shaped in cross section.

4. The intraocular lens assembly of claim 1 wherein said flange further comprises in cross-sectional view a straight portion and a circular portion separated from said periphery of said optic by said straight portion.

\* \* \* \* \*